(12) United States Patent
Weyens et al.

(10) Patent No.: US 7,241,567 B2
(45) Date of Patent: Jul. 10, 2007

(54) T227-1 FLANKING SEQUENCE

(75) Inventors: Guy Weyens, Beersel (BE); Steve Barnes, Petit-Hallet (BE); Inge Rosquin, Lier (BE)

(73) Assignee: SES Europe N.V./S.A., Tiénen (BE)

( * ) Notice: Subject to any disclaimer, the term of this patent is extended or adjusted under 35 U.S.C. 154(b) by 629 days.

(21) Appl. No.: 10/415,602

(22) PCT Filed: Nov. 30, 2001

(86) PCT No.: PCT/GB01/05321

§ 371 (c)(1),
(2), (4) Date: Oct. 2, 2003

(87) PCT Pub. No.: WO02/44407

PCT Pub. Date: Jun. 6, 2002

(65) Prior Publication Data

US 2004/0117870 A1 Jun. 17, 2004

Related U.S. Application Data

(60) Provisional application No. 60/250,110, filed on Nov. 30, 2000.

(51) Int. Cl.
*C12Q 1/68* (2006.01)
(52) U.S. Cl. .................... 435/6; 435/91.1; 435/91.2
(58) Field of Classification Search ............. None
See application file for complete search history.

(56) References Cited

FOREIGN PATENT DOCUMENTS

| EP | 0 218 571 | 4/1987 |
|---|---|---|
| EP | 0 221 044 | 5/1987 |
| EP | 1 167 531 | 1/2002 |
| WO | WO 92/0449 | 3/1992 |
| WO | WO 99/23232 | 5/1999 |
| WO | WO 99/43838 | 9/1999 |
| WO | WO 00/49179 | 8/2000 |
| WO | WO 01/32919 | 5/2001 |
| WO | WO 01/66799 | 9/2001 |
| WO | PCT/GB/01/05321 | 12/2002 |

OTHER PUBLICATIONS

Monnerlop, et al; "Transgenic sugar beet tolerant to glyphosate"; Euphytica, Kluwer Academic Press; vol. 94, No. 1, 1997, pp. 83-91.

*Primary Examiner*—Jeffrey Fredman
*Assistant Examiner*—Heather G. Calamita
(74) *Attorney, Agent, or Firm*—Christensen O'Connor Johnson Kindness PLLC

(57) ABSTRACT

A herbicide resistant transformed sugar beet that is detectable by the specific primers developed to match the DNA sequences that flank the left and/or right border region of the inserted transgenic DNA and the method of identifying primer pairs containing plant genomic DNA/plasmid DNA. More specifically the present invention covers a specific glyphosate resistant sugar beet plant having an insertion of the transgenic material identified as the T227-1 event. The present invention additionally covers primer pairs: plant genomic DNA/Plasmid DNA that are herein identified. Additionally, these primer pairs for either the left or the right flanking regions make an event specific test for the T227-1 insert of transgenic material.

6 Claims, 12 Drawing Sheets

FIGURE 1: Transformation event T227-1 with positions of the specific primers

Diagrammatic interpretation of the Southern blot results.

FIGURE 3
Plasmid sequence at the right border.

RIGHT BORDER sugar beet genome ←→ pMON17227

GATGGCTTCATGTCCATGTGTTTATT | CCCATCAAGCTTGAGCTTCAGGATTTAGCAGCATTC (SEQ ID NO: 1)

| Plasmid sequence (bp) | |
|---|---|
| 7800 | CCTGTGGTTG GCATGCACAT ACAAATGGAC GAACGGATAA ACCTTTTCAC <br>                SUB105 <br> (SEQ ID NO: 2) |
| 7850 | GCCCTTTTAA ATATCCGTTA TTCTAATAAA CGCTCTTTTC TCTTA *GGTTT* <br>                                               RB7 |
| 7900 | ACCCGCCAAT ATATCCTGTC AAACACTGAT AGTTTAAACT GAAGGCGGGA <br>                          RB11     Break at 7965 bp                        RB12 |
| 7950 | AACGACAAATC TGATCCCCAT CAAGCTTGAG⟩CTCAGGATTT AGCAGCATTC <br>                                    SUB106 |
| 8000 | ...219bp.. GCATCATGGT CAGTAAGTTT CAGAAAAA <br> (SEQ ID NO: 3) |

FIGURE 4

Sequence of the right border breakpoint. (SEQ ID NO: 4)

```
GGACAGGACA CGACAGCTCC TCACGAGGTA ATGGATATCA TTAGAGAAAG    50
AGCGGAACAA ATATTACTCA AATGGAGGAT TTATGAAAGT AATAGATATA   100
CTTTACTAGA AAAGGAAGAT TGTCATGATT CAACACCAAA TGACACTTAA   150
ATTAAGAACC CACCTCATCT TAAACCAAAC TAAAATATCA TTTAATACAT   200
ATCCAAGTCA TAATCTACTA GTAGTTTTGC TTGGTGAGAT TACATAATAT   250
ATCACTAATA TATAAGAAAT TTATTTTTCA ATCA AGATCT ATACAACTAA   300
TAACTGAAGT AGGAGAAGAT ATGGGATTGG TGTGGGAGAT GGCTTCATGT   350
CCATGTGTTT ATTCCGATCA AGCTTGAGCT CAGGATTTAG CAGCATTCCA   400
```

98K89 primer — underlined positions ~160-180
BglII restriction site — AGATCT
HindIII restriction site — AGCTT
Integrated plasmid sequence
RB12 primer
Sugarbeet genomic sequence

FIGURE 5

Alignment of the right breakpoint region and the untransformed plant allelic sequence

```
UNTRANSF                                                  ATTTAAATRTC
                                                          * * ******

T227-1 right    AATTAAGAACCCACCTCATCTTAAACCAAACTAAATATC

UNTRANSF        WKTTGMCACATATCCAAGTCATAATCTACKASYAGTTTKG
                **** * ********************************

T227-1 right    ATTTAATACATATCCAAGTCATAATCTACTAGTAGTTTTG

UNTRANSF        CTTGGTGAGATTACATAATATATCACTAATATATATAASAAA
                ******************************************

T227-1 right    CTTGGTGAGATTACATAATATATCACTAATATATATAAGAAA

UNTRANSF        TTTATTTWTCAATCAAGATCTATACAACTAATWMCTGAAG
                ****************************************

T227-1 right    TTTATTTTCAATCAAGATCTATACAACTAATAACTGAAG

UNTRANSF        TAGGAGAAGATATGGGATTGGTGTGTGGGASATGGATTCCCC
                ***************************************

T227-1 right    TAGGAGAAGATATGGGATTGGTGTGTGGGAGATGGCTTCATG

UNTRANSF        ATATAAAGTAAAGAGAGTCAA

T227-1 right    TCCATGTGTTTATTCCCATCAAGCTTGAGCTCAGGATTTA
                17bp fragment        plasmid sequence
```

Plasmid sequence at the left border.

FIGURE 7

Sequence of the left border breakpoint. (SEQ ID NO: 10)

```
Integrated        AATGTNCTTT CATTTTATAA NAAGGCTGCG GACATCTACA TTTTTGAATT   50
plasmid sequence  GANAAAAAAT TGGTAATTAC TCTTTCTTTT TCTCCATATN GACCATCATA  100
LB8 primer        CTCATTGNTG ATCCATGTAG ATTTGCCGGA CATGANGCCA TTTCCCATAT  150
BglII restriction site  CTTCTCCTAC TTCNAGTCNA TTAGTTGTAT AGATCTTGAT TGAAAAATAA  200
                  ATATTTGTCC CAACTCTCTT TTATTCCCTG TGTCCATGTC TGAACAACTT  250
                  TCGAATTTTC TTCCTAATAA TCTCGCGATA ACTTGCATGG TTTGGAACAT  300
                  GCAATGAGCG AGAAATANAA ATTTTATTTC TGCTTTGAAA GCAATTGTTA  350
Sugarbeet         GAATGCATCG TCCTACTGTG ATTGCATGAG TGGAAACACA TATGGAGGA   400
genomic           AATCAAGCTA TGTCTATTGC ATCTGCTCTG GGGTACTCTG GTCATACTCG  450
sequence          TGTCGATGCC ATGGGTTTTT TAGGGGGAAT TTTGATTTAT TGGAAACCAG  500
                  AATTGGTTAC CATAGAACCT ATCATTAGAC ATGCATGATC AACATATAAC  550
                  CATGGAAATA AAAAGGGTAG GGGCTATTCT TTGGTATTTC TCAGCGGTTT  600
                  ATGCGAGTCC CGACCCTACA AAACGCCAAG TTCTTTGGCA AGAATTAAGA  650
HindIII restriction site  AATTTCGCTC GAACTCATAA TCAAGCTTGG CTCATAGCAG GAGATTTTAA  700
                  TGATACCAGA TATTCCTATG AAAGGAATAC TGCTTGTTCG GAAACTCAAC  750
98K86 primer      GTTGTCTCTT AGTTTCAATG ATTGGGTNNN TGACATGGAT TAATGAA     797
```

FIGURE 8

Alignment of the left breakpoint region and the untransformed plant allelic sequence.

| | |
|---|---|
| UNTRANSF | ATATGGGAT-TGGTGTGGGASATGGATTCCCCATAT |
| | \*\*\*  \*\* \* \*\* \* \* \*\*\*   \*\* |
| T227-1 left | AAGCCATTTCCCATATCTTCTCCTACTTCNAGTCN----AT |
| | plasmid sequence      *49bp fragment* |

| | |
|---|---|
| UNTRANSF | AAAGTAAAGAGAGTCAACAAGAAGAWATAAAATATTTGTCC |
| | \* \* \* \*\*\* \* \* \* \*\*\*\*\*\*\* \*\*\*\*\*\*\*\*\* |
| T227-1 left | *TAGTTGTATAGA-TCTTGATTGAAAAATAAA-TATTTGTCC* |

| | |
|---|---|
| UNTRANSF | CAACTCTCTTTTATYCC-TGTGTCCATGTCTGAACAACTYT |
| | \*\*\*\*\*\*\*\*\*\*\*\*\*\*\*\* \*\*\*\*\*\*\*\*\*\*\*\*\*\*\*\*\*\*\*\*\*\* |
| T227-1 left | CAACTCTCTTTTATTCCCTGTGTCCATGTCTGAACAACTTT |

| | |
|---|---|
| UNTRANSF | CGAATTTTCTTCCTAATAATCTCGCGATAACTTGCATGGTT |
| | \*\*\*\*\*\*\*\*\*\*\*\*\*\*\*\*\*\*\*\*\*\*\*\*\*\*\*\*\*\*\*\*\*\*\*\*\*\*\* |
| T227-1 left | CGAATTTTCTTCCTAATAATCTCGCGATAACTTGCATGGTT |

| | |
|---|---|
| UNTRANSF | TGGAACATGCAATGAGCGAGAAATAGAAATTTTATTTCTGC |
| | \*\*\*\*\*\*\*\*\*\*\*\*\*\*\*\*\*\*\*\*\*\*\*\*\*\*\*\*\*\*\*\*\*\*\*\*\*\* |
| T227-1 left | TGGAACATGCAATGAGCGAGAAATANAAATTTTATTTCTGC |

| | |
|---|---|
| UNTRANSF | TTTGAAAGCAATTGTTAGAATGCATCGTCSTACWGTGATTG |
| | \*\*\*\*\*\*\*\*\*\*\*\*\*\*\*\*\*\*\*\*\*\*\*\*\*\*\*\*\*\*\*\*\*\*\*\*\* |
| T227-1 left | TTTGAAAGCAATTGTTAGAATGCATCGTCCTACTGTGATTG |

| | |
|---|---|
| UNTRANSF | CATGAGTGGAAACACATATGGGAGGAAATCAASCTATGTCT |
| | \*\*\*\*\*\*\*\*\*\*\*\*\*\*\*\*\*\*\*\*\*\*\*\*\*\*\*\*\*\*\*\*\*\*\*\*\*\* |
| T227-1 left | CATGAGTGGAAACACATATGGGAGGAAATCAAGCTATGTCT |

| | |
|---|---|
| UNTRANSF | ATTGCATCTGCTCTGGGGTACTCTGGTCATACTCGTGTCGA |
| | \*\*\*\*\*\*\*\*\*\*\*\*\*\*\*\*\*\*\*\*\*\*\*\*\*\*\*\*\*\*\*\*\*\*\*\*\*\* |
| T227-1 left | ATTGCATCTGCTCTGGGGTACTCTGGTCATACTCGTGTCGA |

| | |
|---|---|
| UNTRANSF | TGCCATGGGTTTTTTAGGGGGAATTTTGATWTATTGGAAAC |
| | \*\*\*\*\*\*\*\*\*\*\*\*\*\*\*\*\*\*\*\*\*\*\*\*\*\*\*\*\*\*\*\*\*\*\*\*\*\* |
| T227-1 left | TGCCATGGGTTTTTTAGGGGGAATTTTGATTTATTGGAAAC |

| | |
|---|---|
| UNTRANSF | CAGAATTGGKWRCCATAGAACCTATCATTAGACATGCATGA |
| | ***************************************** |
| T227-1 left | CAGAATTGGTTACCATAGAACCTATCATTAGACATGCATGA |
| | |
| UNTRANSF | TCAACATATAACCATGGAAATAAAAAGGGTWGGGGCTATTC |
| | ***************************************** |
| T227-1 left | TCAACATATAACCATGGAAATAAAAAGGGTAGGGGCTATTC |
| | |
| UNTRANSF | CTTTGGTATTTCTCAGCGGTTTATGCGAGTCCSGACCCTAC |
| | ***************************************** |
| T227-1 left | -TTTGGTATTTCTCAGCGGTTTATGCGAGTCCCGACCCTAC |
| | |
| UNTRANSF | AWAACGCCAAGTTACTTTGGCAAGAATTAAGAAATTTCGCT |
| | ************* ***************************  |
| T227-1 left | AAAACGCCAAGTT-CTTTGGCAAGAATTAAGAAATTTCGCT |
| | |
| UNTRANSF | CGAACTCATWMTCAMGCTKSGCTCATRGCMSGAGAWTTTAA |
| | ***************************************** |
| T227-1 left | CGAACTCATAATCAAGCTTGGCTCATAGCAGGAGATTTTAA |
| | |
| UNTRANSF | TGWK-CCARATKBCCTATGAAAGGAAA |
| | ****  ******** *   **  ** |
| T227-1 left | TGATACCAGATATTCCTATGAAAGGAATACTGCTTGTTCGG |

Legend:
UNTRANSF - SEQ ID NO:11
T277-1 right - SEQ ID NO:12

FIGURE 8 (Continued)

FIGURE 9 Restriction sites of the enzymes on pMON17227.
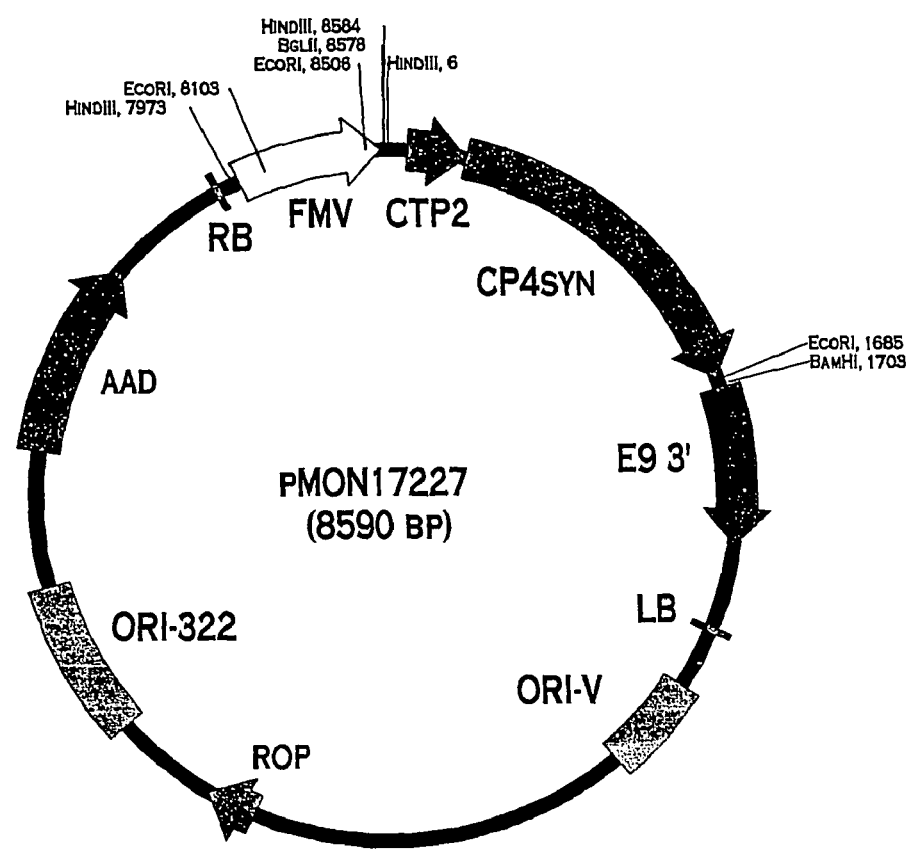

Figure 10a

Sequence of the right border fragment obtained with the 98K89 – RB12 primer set.

(SEQ ID NO: 13)

98K89 primer

AGAACCCACC TCATCTTAAA CCAAACTAAA ATATCATTTA ATACATATCC  50
AAGTCATAAT CTACTAGTAG TTTTGCTTGG TGAGATTACA TAATATATCA  100
CTAATATATA AGAAATTTAT TTTTCAATCA AGATCTATAC AACTAATAAC  150
TGAAGTAGGA GAAGATATGG GATTGGTGTG GGAGATGGCT TCATGTCCAT  200
GTGTTTATTC CCATCAAGCT TGAGCTCAGG ATTTAGCAGC ATTCCA  246

RB12 primer

Figure 10b

Sequence of the right border fragment obtained with the 98K89 – 98I50 primer set.

(SEQ ID NO: 14)

98K89 primer

AGAACCCACC TCATCTTAAA CCAAACTAAA ATATCATTTA ATACATATCC  50
AAGTCATAAT CTACTAGTAG TTTTGCTTGG TGAGATTACA TAATATATCA  100
CTAATATATA AGAAATTTAT TTTTCAATCA AGATCTATAC AACTAATAAC  150
TGAAGTAGGA GAAGATATGG GATTGGTGTG GGAGATGGCT TCATGTCCAT  200
GTGTTTATTC CCATCAAGCT TGAGCTCAGG ATTTAGCAGC ATTCCAGATT  250
GGGTTCAATC AACAAGGTAC GAGCCATATC ACTTTATTCA AATTGGTATC  300
GCCAAAACCA AGAAGGAACT CCCATCCTCA AAGGTTTGTA AGGAAGAATT  350
CTCAGTCCAA AGCCTCAACA AGGTCAGGGT ACAGAGTCTC CAAACCATTA  400
GCCAAAAGCT ACAGGAGATC AATGAAGAAT CTTCAATCAA AGTAAACTAC  450
TGTTCCAGCA CATGCATCAT GGTCAG  476

Figure 10c

Sequence of the left border fragment obtained with the 98G94 – 98K86 primer set.

(SEQ ID NO: 15)

98G94 primer

```
CGCCTATAAA TACGACGGAT CGTAATTTGT CGTTTTATCA AAATGTACTT  50
TCATTTTATA ATAACGCTGC GGACATCTAC ATTTTTGAAT TGAAAAAAAA  100
TTGGTAATTA CTCTTTCTTT TTCTCCATAT TGACCATCAT ACTCATTGCT  150
GATCCATGTA GATTTCCCGG ACATGAAGCC ATTTCCCATA TCTTCTCCTA  200
CTTCNAGTCN ATTAGTTGTA TAGATCTTGA TTGAAAAATA AATATTTGTC  250
CCAACTCTCT TTTATTCCCT GTGTCCATGT CTGAACAACT TTCGAATTTT  300
CTTCCTAATA ATCTCGCGAT AACTTGCATG GTTTGGAACA TGCAATGAGC  350
GAGAAATANA AATTTTATTT CTGCTTTGAA AGCAATTGTT AGAATGCATC  400
GTCCTACGTG ATTGCATGAG TGGAAACACA TATGGGAGGA AATCAAGCTA  450
TGTCTATTGC ATCTGCTCTG GGTACTCTG GTCATACTCG TGTCGATGCC  500
ATGGGTTTTT TAGGGGGAAT TTTGATTTAT TGGAAACAGA ATTGGTTACC  550
ATAGAACCTA TCATTAGACA TGCATGATCA ACATATAACC ATGGAAATAA  600
AAAGGGTAGG GGCTATTCTT TGGTATTTCT CAGCGGTTTA TGCGAGTCCC  650
GACCCTACAA AACGCCAAGT TCTTTGGCAA GAATTAAGAA ATTTCGCTCG  700
AACTCATAAT CAAGCTTGGC TCATAGCAGG AGATTTTAAT GATACCAGAT  750
ATTCCTATGA AAGGAATACT GCTTGTTCGG AAACTCAACG TT          792
```

98K86 primer

SEQUENCE LISTING

```
<160> NUMBER OF SEQ ID NOS: 15

<210> SEQ ID NO 1
<211> LENGTH: 61
<212> TYPE: DNA
<213> ORGANISM: Artificial Sequence
<220> FEATURE:
<223> OTHER INFORMATION: Description of Artificial Sequence: Plasmid
                        sequence at the right border

<400> SEQUENCE: 1
gatggcttca tgtccatgtg tttattccca tcaagcttga gctcaggatt tagcagcatt      60
c                                                                      61

<210> SEQ ID NO 2
<211> LENGTH: 200
<212> TYPE: DNA
<213> ORGANISM: Artificial Sequence
<220> FEATURE:
<223> OTHER INFORMATION: Description of Artificial Sequence: Plasmid
                        sequence at the right border

<400> SEQUENCE: 2
cctgtggttg gcatgcacat acaaatggac gaacggataa acctttcac gcccttttaa       60 atatccgtta ttctaataaa cgctcttttc tcttaggttt acccgccaat atatcctgtc     120
aaacactgat agtttaaact gaaggcggga aacgacaatc tgatccccat caagcttgag     180
ctcaggattt agcagcattc                                                 200

<210> SEQ ID NO 3
<211> LENGTH: 28
<212> TYPE: DNA
<213> ORGANISM: Artificial Sequence
```

```
<220> FEATURE:
<223> OTHER INFORMATION: Description of Artificial Sequence: Plasmid
      sequence at the right border

<400> SEQUENCE: 3
gcatcatggt cagtaagttt cagaaaaa                                         28

<210> SEQ ID NO 4
<211> LENGTH: 400
<212> TYPE: DNA
<213> ORGANISM: Artificial Sequence
<220> FEATURE:
<223> OTHER INFORMATION: Description of Artificial Sequence: Sequence of
      the right border breakpoint

<400> SEQUENCE: 4
ggacaggaca cgacagctcc tcacgaggta atggatatca ttagagaaag agcggaacaa      60
atattactca aatggaggat ttatgaaagt aatagatata ctttactaga aaaggaagat     120
tgtcatgatt caacaccaaa tgacacttaa attaagaacc cacctcatct taaaccaaac     180
taaaatatca tttaatacat atccaagtca taatctacta gtagttttgc ttggtgagat     240
tacataatat atcactaata tataagaaat ttattttca atcaagatct atacaactaa      300
taactgaagt aggagaagat atgggattgg tgtgggagat ggcttcatgt ccatgtgttt     360
attcccatca agcttgagct caggatttag cagcattcca                           400

<210> SEQ ID NO 5
<211> LENGTH: 192
<212> TYPE: DNA
<213> ORGANISM: Beta vulgaris

<400> SEQUENCE: 5
atttaaatrt cwkttgmcac atatccaagt cataatctac kasyagttk gcttggtgag       60 attacataat akatcactaa tatataasaa atttatttwt caatcaagat ctatacaact     120
aatwmctgaa gtaggagaag atatgggatt ggtgtgggas atggattccc catataaagt     180
aaagagagtc aa                                                         192

<210> SEQ ID NO 6
<211> LENGTH: 240
<212> TYPE: DNA
<213> ORGANISM: Artificial Sequence
<220> FEATURE:
<223> OTHER INFORMATION: Description of Artificial Sequence: Transformed
      sugar beet T227-1

<400> SEQUENCE: 6
aattaagaac ccacctcatc ttaaaccaaa ctaaaatatc atttaataca tatccaagtc      60
ataatctact agtagttttg cttggtgaga ttacataata tatcactaat atataagaaa     120 tttattttc aatcaagatc tatacaacta ataactgaag taggagaaga tatgggattg     180
gtgtgggaga tggcttcatg tccatgtgtt tattcccatc aagcttgagc tcaggattta     240

<210> SEQ ID NO 7
<211> LENGTH: 56
<212> TYPE: DNA
<213> ORGANISM: Artificial Sequence
<220> FEATURE:
<223> OTHER INFORMATION: Description of Artificial Sequence: Plasmid
      sequence at the left border
```

-continued

<210> SEQ ID NO 7

<400> SEQUENCE: 7
ctgatccatg tagatttccc ggacatgaag ccatttccca tatcttctcc tacttc      56

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Plasmid
      sequence at the left border

<400> SEQUENCE: 8
aattgattga caacatgcat caatcgacct g      31

<210> SEQ ID NO 9
<211> LENGTH: 160
<212> TYPE: DNA
<213> ORGANISM: Artificial Sequence
<220> FEATURE:
<223> OTHER INFORMATION: Description of Artificial Sequence: Plasmid
      sequence at the left border

<400> SEQUENCE: 9
ctgatccatg tagatttccc ggacatgaag ccatttacaa ttgaatatat cctgccgccg      60
ctgccgcttt gcacccggtg gagcttgcat gttggtttct acgcagaact gagccggtta     120
ggcagataat ttccattgag aactgagcca tgtgcacctt                           160

<210> SEQ ID NO 10
<211> LENGTH: 797
<212> TYPE: DNA
<213> ORGANISM: Artificial Sequence
<220> FEATURE:
<223> OTHER INFORMATION: Description of Artificial Sequence: Sequence of
      the left border breakpoint
<220> FEATURE:
<221> NAME/KEY: misc_feature
<222> LOCATION: 6, 21, 53, 90, 108, 136, 164, 169, 318, 778..780
<223> OTHER INFORMATION: n = any base

<400> SEQUENCE: 10
aatgtncttt cattttataa naacgctgcg gacatctaca tttttgaatt ganaaaaaat      60
tggtaattac tctttctttt tctccatatn gaccatcata ctcattgntg atccatgtag     120
atttcccgga catgangcca tttcccatat cttctcctac ttcnagtcna ttagttgtat     180
agatcttgat tgaaaaataa atatttgtcc caactctctt ttattccctg tgtccatgtc     240
tgaacaactt tcgaattttc ttcctaataa tctcgcgata acttgcatgg tttggaacat     300
gcaatgagcg agaaatanaa attttatttc tgctttgaaa gcaattgtta gaatgcatcg     360
tcctactgtg attgcatgag tggaaacaca tatgggagga aatcaagcta tgtctattgc     420
atctgctctg gggtactctg gtcatactcg tgtcgatgcc atgggttttt taggggaat      480 tttgatttat tggaaaccag aattggttac catagaacct atcattagac atgcatgatc     540
aacatataac catggaaata aaagggtag gggctattct ttggtatttc tcagcggttt      600
atgcgagtcc cgaccctaca aaacgccaag ttctttggca agaattaaga aatttcgctc     660
gaactcataa tcaagcttgg ctcatagcag gagattttaa tgataccaga tattcctatg     720
aaaggaatac tgcttgttcg gaaactcaac gttgtctctt agtttcaatg attgggtnnn     780
tgacatggat taatgaa                                                    797

<210> SEQ ID NO 11
<211> LENGTH: 593
<212> TYPE: DNA
<213> ORGANISM: Beta vulgaris

<400> SEQUENCE: 11

| | | | |
|---|---|---|---|
| atatgggatt ggtgtgggas atggattccc catataaagt aaagagagtc aacaagaaga | 60 |
| wataaaatat ttgtcccaac tctcttttat ycctgtgtcc atgtctgaac aactytcgaa | 120 |
| ttttcttcct aataatctcg cgataacttg catggtttgg aacatgcaat gagcgagaaa | 180 |
| tagaaatttt atttctgctt tgaaagcaat tgttagaatg catcgtcsta cwgtgattgc | 240 |
| atgagtggaa acacatatgg gaggaaatca asctatgtct attgcatctg ctctggggta | 300 |
| ctctggtcat actcgtgtcg atgccatggg tttttaggg ggaattttga twtattggaa | 360 |
| accagaattg gkwrccatag aacctatcat tagacatgca tgatcaacat ataaccatgg | 420 |
| aaataaaaag ggtwggggct attcctttgg tatttctcag cggtttatgc gagtccsgac | 480 |
| cctacawaac gccaagttac tttggcaaga attaagaaat ttcgctcgaa ctcatwmtca | 540 |
| mgctksgctc atrgcmsgag awtttaatgw kccaratkbc ctatgaaagg aaa | 593 |

<210> SEQ ID NO 12
<211> LENGTH: 607
<212> TYPE: DNA
<213> ORGANISM: Artificial Sequence
<220> FEATURE:
<223> OTHER INFORMATION: Description of Artificial Sequence: Transformed
       sugar beet T227-1
<220> FEATURE:
<221> NAME/KEY: misc_feature
<222> LOCATION: 30, 35, 184
<223> OTHER INFORMATION: n = any base

<400> SEQUENCE: 12

| | | | |
|---|---|---|---|
| aagccatttc ccatatcttc tcctacttcn agtcnattag ttgtatagat cttgattgaa | 60 |
| aaataaatat ttgtcccaac tctcttttat tccctgtgtc catgtctgaa caactttcga | 120 |
| attttcttcc taataatctc gcgataactt gcatggtttg gaacatgcaa tgagcgagaa | 180 |
| atanaaattt tatttctgct tgaaagcaa ttgttagaat gcatcgtcct actgtgattg | 240 |
| catgagtgga acacatatg ggaggaaatc aagctatgtc tattgcatct gctctggggt | 300 |
| actctggtca tactcgtgtc gatgccatgg gtttttagg gggaattttg atttattgga | 360 |
| aaccagaatt ggttaccata gaacctatca ttagacatgc atgatcaaca tataaccatg | 420 |
| gaaataaaaa gggtagggc tattctttgg tatttctcag cggtttatgc gagtcccgac | 480 |
| cctacaaaac gccaagttct ttggcaagaa ttaagaaatt tcgctcgaac tcataatcaa | 540 |
| gcttggctca tagcaggaga ttttaatgat accagatatt cctatgaaag gaatactgct | 600 |
| tgttcgg | 607 |

<210> SEQ ID NO 13
<211> LENGTH: 246
<212> TYPE: DNA
<213> ORGANISM: Artificial Sequence
<220> FEATURE:
<223> OTHER INFORMATION: Description of Artificial Sequence: Sequence of
       the right border fragment obtained with the
       98K89 - RB12 primer set

<400> SEQUENCE: 13

| | | | |
|---|---|---|---|
| agaacccacc tcatcttaaa ccaaactaaa atatcattta atacatatcc aagtcataat | 60 |
| ctactagtag ttttgcttgg tgagattaca taatatatca ctaatatata agaaatttat | 120 |

```
ttttcaatca agatctatac aactaataac tgaagtagga gaagatatgg gattggtgtg      180
ggagatggct tcatgtccat gtgtttattc ccatcaagct tgagctcagg atttagcagc      240
attcca                                                                246
```

```
<210> SEQ ID NO 14
<211> LENGTH: 476
<212> TYPE: DNA
<213> ORGANISM: Artificial Sequence
<220> FEATURE:
<223> OTHER INFORMATION: Description of Artificial Sequence: Sequence of
                        the right border fragment obtained with the
                        98K89 - 98150 primer set

<400> SEQUENCE: 14
```

```
agaacccacc tcatcttaaa ccaaactaaa atatcattta atacatatcc aagtcataat       60
ctactagtag ttttgcttgg tgagattaca taatatatca ctaatatata agaaatttat      120
ttttcaatca agatctatac aactaataac tgaagtagga gaagatatgg gattggtgtg      180
ggagatggct tcatgtccat gtgtttattc ccatcaagct tgagctcagg atttagcagc      240
attccagatt gggttcaatc aacaaggtac gagccatatc actttattca aattggtatc      300
gccaaaacca agaaggaact cccatcctca aaggtttgta aggaagaatt ctcagtccaa      360
agcctcaaca aggtcagggt acagagtctc caaaccatta gccaaaagct acaggagatc      420
aatgaagaat cttcaatcaa agtaaactac tgttccagca catgcatcat ggtcag         476
```

```
<210> SEQ ID NO 15
<211> LENGTH: 792
<212> TYPE: DNA
<213> ORGANISM: Artificial Sequence
<220> FEATURE:
<223> OTHER INFORMATION: Description of Artificial Sequence: Sequence of
                        the left border fragment obtained with the
                        98G94 - 98K86 primer set
<220> FEATURE:
<221> NAME/KEY: misc_feature
<222> LOCATION: 205, 210, 359
<223> OTHER INFORMATION: n = any base

<400> SEQUENCE: 15
```

```
cgcctataaa tacgacggat cgtaatttgt cgttttatca aaatgtactt tcattttata       60
ataacgctgc ggacatctac atttttgaat tgaaaaaaaa ttggtaatta ctctttcttt      120
ttctccatat tgaccatcat actcattgct gatccatgta gatttcccgg acatgaagcc      180
atttcccata tcttctccta cttcnagtcn attagttgta tagatcttga ttgaaaaata      240
aatatttgtc ccaactctct tttattccct gtgtccatgt ctgaacaact ttcgaatttt      300
cttcctaata atctcgcgat aacttgcatg gtttggaaca tgcaatgagc gagaaatana      360 aattttatt ctgctttgaa agcaattgtt agaatgcatc gtcctacgtg attgcatgag      420
tggaaacaca tatgggagga aatcaagcta tgtctattgc atctgctctg gggtactctg      480
gtcatactcg tgtcgatgcc atgggttttt tagggggaat tttgatttat tggaaacaga      540
attggttacc atagaaccta tcattagaca tgcatgatca acatataacc atggaaataa      600
aaagggtagg ggctattctt tggtatttct cagcggttta tgcgagtccc gaccctacaa      660
aacgccaagt tctttggcaa gaattaagaa atttcgctcg aactcataat caagcttggc      720
tcatagcagg agattttaat gataccagat attcctatga aaggaatact gcttgttcgg      780
aaactcaacg tt                                                          792
```

T227-1 FLANKING SEQUENCE

CROSS REFERENCES TO RELATED APPLICATIONS

This application claims the benefit under 35 U.S. C. §371 as a national filing of the international application Number PCT/ GB01/05321 filed 30 Nov. 2001 and claims the benefit of the U.S. provisional application No. 60/250,110 filed 30 Nov. 2000.

FIELD OF THE INVENTION

The field of the invention broadly covers a herbicide resistant transformed sugar beet that is detectable by the specific primers developed to match the DNA sequences that flank the left and/or right border region of the inserted transgenic DNA and the method of identifying primer pairs containing plant genomic DNA/plasmid DNA. More specifically the present invention covers a specific glyphosate resistant sugar beet plant having an insertion of the transgenic material identified as the T227-1 event. The present invention additionally covers primer pairs: plant genomic DNA/Plasmid DNA that are herein identified. Additionally, these primer pairs for either the left or the right flanking regions make an event specific test for the T227-1 insert of transgenic material. These event specific tests using the primers include a method that employs electrophoresis through gels as the standard method used to separate, identify and purify DNA fragments. The location of the DNA that are separated by size within the gels can be determined by using a dye. This dye permits DNA bands with 1–10 ng of DNA to be detected under ultraviolet light.

BACKGROUND

In the last few years there has been numerous commercial products having glyphosate resistance plants such as soybeans, maize, and rapeseed. At least two different genes have been used to make these commercial products. These products have had a specific event which has been developed through extensive research and testing and then registered with the regulatory authorities in the various countries as genetically modified organisms.

The regulatory requirements in Europe for introduction of plants that have had foreign DNA introduced are most stringent. Although not a specific requirement regulatory offices favor inserted events containing DNA which is necessary for the expression of the introduced trait and very little extra DNA in the insert. On the practical side, the event should have low numbers of copies to avoid problems with gene silencing. Development of these types of insertion events in certain crops such as sugar beets can be difficult. The inserted event should provide the plant with the desired levels of gene expression such as resistance to the application of a herbicide, resistance to insect attack, or production of an oil or sugar, and the like.

Additionally, there is the need to have an insert in sugar beet that is identifiable through tests developed for the inserted event. These test results can be employed to track the GMO in production plants and fields.

There is a need to be able to clearly identify a transgenic plant through its inserted DNA. The need for identifiable transgenic events and the primers and the event specific tests for these primers are increasingly evident.

SUMMARY OF THE INVENTION

Broadly the present invention is to a method of detecting a glypho sate resistant sugar beet comprising the steps of forming primers that flank the genomic and plasmid sequence border in the sugar beet which can uniquely identify the sugar beet, by using a PCR to sequence the unique fragment produced by the primers and detecting the absence or presence of the fragment. The present invention covers a glyphosate resistant sugar beet detectable by this method. Additionally this invention covers a transgenic glyphosate resistant sugar beet comprising an insertion of DNA unique to T227-1 and its progeny. This invention is detectable by either of the pair of primers for the left or right border. The primer set capable of generating a DNA fragment unique to identify T227-1 of 50 base pairs and more preferably approximately 100 base pairs. Wherein the DNA fragment unique to identify T227-1 includes some base pairs related to the sugarbeet genomic DNA and some base pairs related to the inserted plasmid DNA (from pMon17227 in T227-1. A sugar beet that is detectable with a pair of primers in accordance with the present invention that border the left flanking sequence identified as 98G94 (nucleotides 1–20 of SEQ ID NO: 15) and 98K86 (nucleotides 730–753 of SEQ ID NO: 10) generating a 792 bp fragment (SEQ ID NO: 15).

A sugar beet is also detectable with the pair of primers that border the right flanking sequence identified as 98I50 (nucleotides 455–476 of SEQ ID NO: 14) and 98K89 (nucleotides 155–180 of SEQ ID NO: 4) generating a 476 bp fragment (SEQ ID NO: 14). Or the primer set 98K89 (nucleotides 155–179 of SEQ ID NO: 4)–RB12 (nucleotides 185–200 of SEQ ID NO: 2) can also be employed to produce a unique fragment of 246 base pairs (SEQ ID) NO: 13).

The invention also includes the pairs of primers comprising DNA which flank at least one of the border regions of the insertion of DNA into the T227-1 Event.

The T227-1 event is sugarbeet material that is capable of glyphosate resistance when in the plant form and is capable of being detected by at least one of the pair of primers 98G94 (nucleotides 1–20 of SEQ ID NO: 15) and 98K86 (nucleotides 730–753 of SEQ ID NO: 10), 98I50 (nucleotides 455–476 of SEQ ID NO: 14) and 98K89 (nucleotides 155–180 of SEQ ID NO: 4), and/or 98K89 (nucleotides 155–180 of SEQ ID NO: 4)–RB12 (nucleotides 185–200 of SEQ ID NO: 2). The primers should when a positive result is produced identify a DNA fragment or a fragment of a length not associated with the primers. The invention has identified a pair of primers comprising DNA which lies in right border region of insertion of DNA into the T227-1 Event wherein one primer lies in the plant genomic material and the other primer is in the inserted plasmid material.

The invention has also identified a pair of primers comprising DNA which lies in the left border region (FIG. 6) of insertion of DNA into the T227-1 Event wherein one primer lies in the plant genomic material and the other primer is in the inserted plasmid material.

The primers themselves are generated to identify the T227-1 event by employing a PCR test using a pair of primers. The primers are used in a PCR method to detect the presence or absence of the T227-1 event. A test kit for the T227-1 event can be formed with the primers as components thereof.

The method of detecting the T227-1 event including the steps of selecting sugar beet genomic material for testing; employing at least one of the pair of primers capable of detecting the T227-1 event in association with such selected material; and using a PCR machine to amplify the DNA fragment if it exists; detecting the presence or the absence of the DNA fragment.

The transgenic glyphosate resistant sugar beet of the present invention is characterized by an unique sequence of DNA having at least 80% homology to the right border sequence in FIG. 3 (SEQ ID NO: 2) or the left border sequence in FIG. 6 (SEQ ID NO: 9) comprising genomic sugar beet DNA proximate the breakpoint of the insertion of the DNA into the genome and inserted plasmid DNA.

This invention encompasses a transgenic glyphosate resistant sugar beet wherein at least a 10–20 base pair fragment of said sequence of DNA is capable of detection by a pair of flanking primers wherein one of said primers is developed from the genomic sugar beet DNA proximate the breakpoint of the insertion of the DNA into the genome and one of said primers being developed from the inserted DNA plasmid.

BRIEF DESCRIPTION OF THE FIGURES

FIG. 3 shows the plasmid sequence at the right border identified as SEQ ID NOS: 1, 2 and 3.

FIG. 4 shows the sequence of the right border breakpoint shown in SEQ ID NO: 4.

FIG. 5 shows the alignment of the right breakpoint region in the transformed sugarbeet T227-1 shown in SEQ ID NO: 6 with the untransformed plant allelic sequence shown in SEQ ID NO: 5.

FIG. 7 shows the sequence of the left border breakpoint between the sugar beet genomic material and the inserted plasmid material shown in SEQ ID NO: 10.

FIG. 8 shows the alignment of the left breakpoint region shown in SEQ ID NO: 12 and the untransformed plant allelic sequence shown in SEQ ID NO: 11.

FIG. 9 shows the plasmid pMON17227.

FIG. 10a shows the sequence of the right border fragment obtained with the 98K89–RB12 primer set identified as SEQ ID NO: 13.

FIG. 10b shows the sequence of the right border fragment obtained with the 98K89–98I50 primer set identified as SEQ ID NO: 14.

FIG. 10c shows the sequence of the left border fragment obtained with the 98G94–98K86 primer set identified as SEQ ID NO: 15.

DETAILED DESCRIPTION OF THE INVENTION

Figure 1:
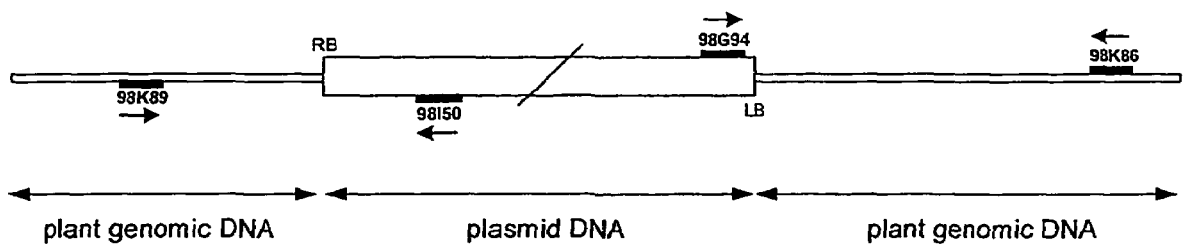
FIG. 1 shows the primers used in the flanking PCR test.

The selection of a specific event in sugar beets (*Beta vulgaris*) requires the production of numerous transformants. These transformants must be screened in most instances to eliminate those transformants that do not conform fairly closely with the genotype of the original germplasm employed. These transformants must be tested for the efficiency of the inserted event. On a molecular basis these transformants must be tested for copy number to mostly to select for low copy number which may avoid gene silencing. Additionally, the transformants are tested and developed and screened based on the positional effect the location in the genome the inserted event has on the gene activity. Different insertion sites in the genome results in different overall results. For example, if the insertion is located in an area with high transcription there may be many copies of the protein produced; if the insertion is located in an area with low transcription, the protein may not be produced at sufficient levels for the desired gene effect. Thus, the selection of an insertion in recalcitrant plant such as sugar beet involves numerous levels of investigative work and research. This type of research and development differs from plant to plant, from gene to gene, and according to the desired results.

The present invention broadly encompasses a sugar beet which is resistant to glyphosate at levels that would normally result in the death of the sugar beet plant. The resistance has been introduced by the *Agrobacterium* mediated transformation of the sugar beet with the pMON17227 plasmid. This plasmid is shown in FIG. 9 and it contains the FMV 35S promoter. The 35 S promoter is from a modified figwort mosaic virus. It also contains the chloroplast transit peptide from the EPSPS gene of *Arabidopsis*. And the CP4 synthetic gene optimized from the 5-enolpyruvylshikimate-3-phosphate synthase (CP4 EPSPS) gene from *Agrobacterium* sp. Strain CP4. This plasmid also contains the terminator from pea. The terminator is from the pea gene RBCSE9. The E9 3' is the pea rbcS (small subunit ribulose bisphosphate carboxylase oxygenase) E9 gene. The plasmid also includes the left and right T-DNA border sequences from *Agrobacterium*.

Numerous transformants were produced by the *Agrobacterium* mediated transformation of the sugar beet. The plantlets that survived the initial transformation stages were then screened in a green house for herbicide resistance. Levels of differing doses of herbicide were applied to the plant to determine which transformants were sensitive and which were resistant. The sensitive transformants were destroyed by the herbicide application and the resistant plants were subjected to further analysis based on comparison to the genome of the original germplasm employed in the transformation process. The transformants that were not eliminated in this screening were further selected from in further green house experiments. The resulting selected transgenic plants were analysed on a different criteria including on the molecular level.

This analysis led to the selection of a rare event insertion designated T227-1. The transformation method used to generate T227-1 integrated the vector into the genome by breakage of the circular vector at a position that was relative to the left and right border sequences. In the *Agrobacterium* system, the left and right border sequences are specifically recognised by vir genes (virD1 and virD2). These proteins produce nicks in the border sequences and the fragment is transferred from the bacterial cell into the plant cell as a single stranded T-DNA molecule, not as a circular vector.

To characterise T227-1 fully, as well as providing information that could serve as a basis for event-specific PCR tests, the nucleotide sequence of the breakpoints between inserted vector and plant genomic DNA was determined.

Flanking Sequences—T227-1

Genomic sequences flanking the T227-1 insert were isolated by linker PCR. Genomic DNA was digested with restriction endonucleases and linkers attached to the ends of the fragments obtained. The fragments containing the T227-1 sequences were preferentially amplified by PCR using the linker sequence and pMON17227-specific sequences as primers. The PCR products were sequenced directly, and the sequences used to design further primers, which were used to amplify plant genomic DNA from T227-1 and from untransformed plants.

Genomic plant DNA fragments were isolated for both left and right borders. These linker PCR products were sequenced and these sequences were aligned with (a) pMON17227 and (b) the fragments generated by the plant genomic primers using plant DNAs (containing the transformed and untransformed "alleles") as templates.

Although the sequence contains some ambiguities, these are essentially consistent with the sequences being identical.

Right Breakpoint

The present invention has its sugar beet genetic makeup at the insert sites in the right and left border regions identified and defined. In FIG. 3 the plasmid sequence at the right border is shown (SEQ ID NO: 2). The inserted DNA sequence was from pMON17227. The top portion of the drawing shows the sequence of the right border of the insert, the sugar beet genome and the beginning of the inserted foreign DNA (SEQ ID NO: 1). The Sub 105, the RB7 and the RB11 are small primer regions (nucleotides 5–22, 103–119 and 156–180, respectively, of SEQ ID NO: 2). The various combinations of primer regions can be employed singly or in pairs. The break at 7965 base pairs (indicated by the arrow) shows where the insertion has occurred. The DNA before this break is genomic sugar beet and after the break is the sequence from the plasmid.

FIG. 4 shows the sequence of the right border breakpoint and where the primers lie on this sequence (SEQ ID NO: 4). In the fourth row of sequence data the bolded sequence indicates the DNA sequence of the 98K89 primer (nucleotides 155–180 of SEQ ID NO: 4). The bolded sequence in the sixth line of sequence indicates the restriction site of BglII (nucleotides 285–290 of SEQ ID NO: 4). The sequence that is in the greyed in area is the beginning of the integrated plasmid material from pMON17227 (nucleotides 364–400 of SEQ ID NO: 4). Within the greyed are two separate bolded portions of sequence. The first bolded sequence portion is the HindIII restriction site (nucleotides 370–375 of SEQ ID NO: 4). The second bolded sequence portion is the RB12 primer sequence (nucleotides 383–400 of SEQ ID NO: 4). The pair of primers, when employed, allow the PCR fragment of DNA that is also unique to this event to be generated.

FIG. 5 shows the alignment of the right breakpoint region in the transformed sugar beet T227-1 (SEQ ID NO: 6) with the untransformed plant allelic sequence (SEQ ID NO: 5). The sequence matches up so that it shows that the gene in the untransformed plant and the T227-1 event match. Certain base pairs could not be identified as ACTG and the following classification was used as listed in Table 1.

TABLE 1

| |
|---|
| S = G or C |
| R = A or G |
| W = A or T |
| K = G or T |
| M = A or C |
| Y = C or T |
| N = any base |
| B = C, G or T |

There is a 17 base pair fragment (nucleotides 198–214 of SEQ ID NO: 6) in the last line of the sequence before the start of the plasmid sequence that indicates that there are 17 base pairs in the T227-1 transformed sugar beet that differs from the untransformed. After this 17 base pair fragment, which is in italics, the plasmid sequence data is found (nucleotides 215–240 of SEQ ID NO: 6).

The alignments of sequence data at the right side of the integration site are shown in FIG. 5. The nucleotides common to both the transformant (T227-1) and the plasmid (pMON17227) are indicated by an asterisk (*) below the aligned sequence.

Between the vector breakpoint and the beginning of homology with beet genomic sequences, a 17 bp fragment is found which is not present in the untransformed allelic sequences studied in this germplasm. (nucleotides 198–214 of SEQ ID NO: 6). No perfect homology could be found between this short unknown DNA sequence and the plasmid sequence.

These results are entirely consistent with the Southern and PCR analyses of T227-1.

Left Breakpoint

Figure 6:
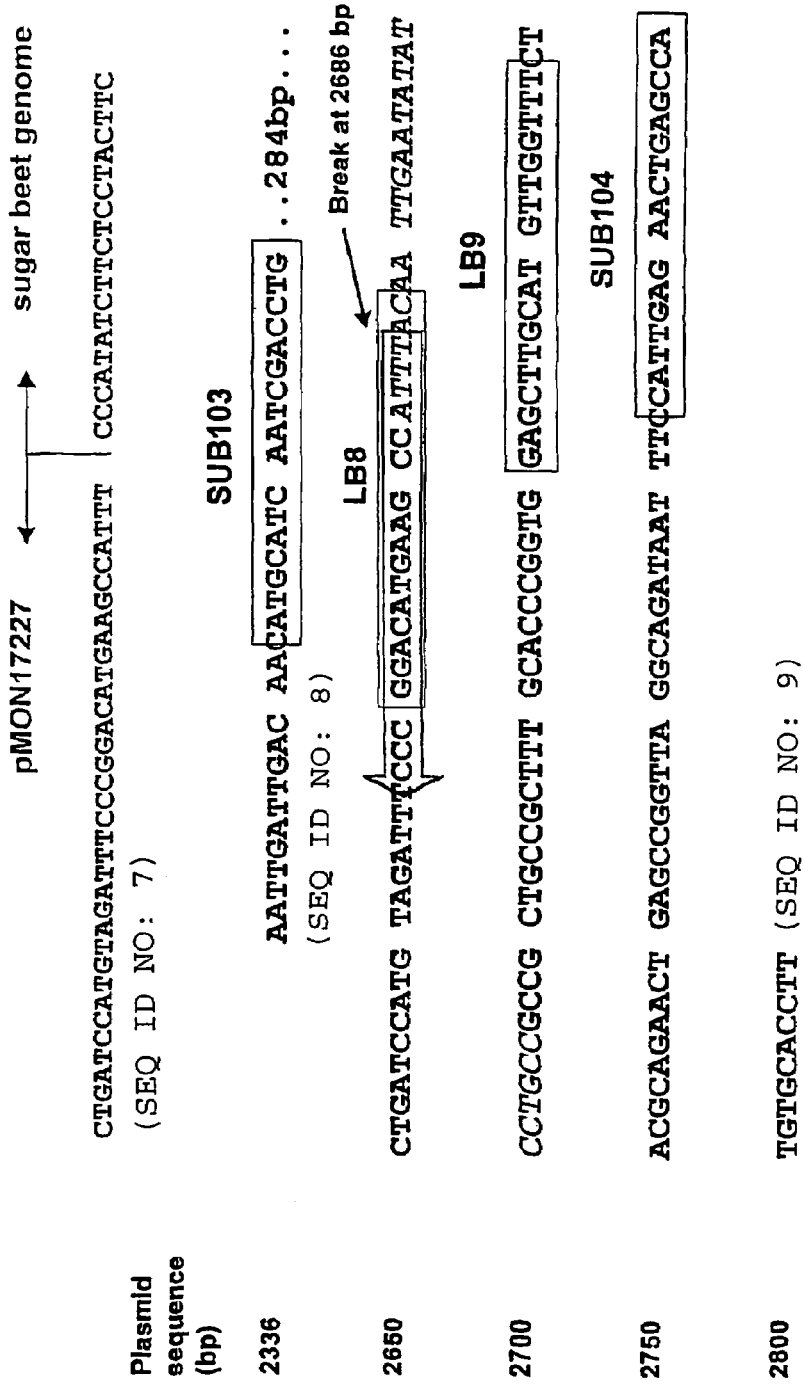
FIG. 6 shows the plasmid sequence at the left border identified as SEQ ID NOS: 7, 8 and 9.

FIG. 6 shows the plasmid sequence at the left border (SEQ ID NO: 9). The inserted DNA sequence was from pMON17227. The top portion of the drawing shows the sequence of the left border of the insert and the associated sugar beet genome (SEQ ID NO: 7). The base pair 2336 is a portion of the left border of the inserted DNA material (SEQ ID NO: 8). The Sub 103 (nucleotides 13–30 of SEQ ID NO: 8), Sub 104 (nucleotides 134–150 of SEQ ID NO: 9), LB8 (nucleotides 21–36 of SEQ ID NO: 9) and the LB9 (nucleotides 81–98 of SEQ ID NO: 9) are small primer regions. The break at 2686 base pairs (indicated by the arrow) shows where the insert border has occurred. The DNA before this break is the sequence from the plasmid and after the break is genomic sugar beet.

FIG. 7 shows the sequence of the left border breakpoint between the sugar beet genomic material and the inserted plasmid material (SEQ ID NO: 10). The greyed in region is the integrated plasmid sequence (nucleotides 1–143 of SEQ ID NO: 10). At the end of this sequence is the bolded primer LB8 (nucleotides 128–143 of SEQ ID NO: 10). In the next line is the bolded sequence that indicates the restriction site for BglII (nucleotides 181–186 of SEQ ID NO: 10). The primer that is located in the sugar beet genomic material is identified in bold in the figure at the bottom (nucleotides 730–753 of SEQ ID NO: 10).

FIG. 8 shows the alignment of the left breakpoint region (SEQ ID NO: 12) and the untransformed plant allelic sequence (SEQ ID NO: 11). The T227-1 transformed event starts with the plasmid sequence. Then there is a region of sparse matching between the untransformed and the T227-1, a fragment of 49 base pairs (nucleotides 10–58 of SEQ ID NO: 12). Thereafter there is a close correlation between the untransformed sugar beet and the transformed sugar beet called event T227-1.

The alignments of sequences from the left side of the integration site and its known component elements are shown in FIG. 8.

At the 3' end of the sequence there is clear homology to the pMON17227 vector though there is a 49 base pair fragment (nucleotides 10–58 of SEQ ID NO: 12) that sparsely aligns with the untransformed beet "allele", or to pMON17227.

On the basis of the sequence shared by the transformant and the plasmid it is clear that a 4 base pair section of the left T-DNA border was incorporated into the Event T227-1 during or following the transformation event. No right T-DNA border and very little of the left T-DNA border portions, were integrated into the transgenic sugar beet event entitled T227-1.

Beyond this 4 base pair section of the left T-DNA border region from *Agrobacterium* the plasmid sequence has been entirely integrated, excluding the right border section of the Agrobacterium region, after which point recombination has taken place to insert the construct into the beet genome.

These results are fully consistent with the Southern hybridisation results.

Use of Flanking Primers to Analyse T227-1 and Untransformed Sugar Beets

Specific primers were developed from the left and right flanking sequences, and used in PCR reactions with each other or individually with primers from within the insert. Primer locations in the inserted DNA and in the sequence flanking the insert are shown in FIGS. 1, 3–7 and Table 1.

PCR reactions between a flanking primer and an insert primer always gave the size expected from the sequence information, and have never given any product in untransformed beet or transformants other than T227-1. Thus these sequences are used as an event-specific test whereby the T227-1 event is identified. This identification process of the insertion of event T227-1 which is one copy and has little extraneous DNA and is highly efficacious at resisting the effects of glyphosate on the plant, is possible in the original germplasm and in progeny developed by any manner of breeding or selfing. The material from the progeny including pollen and seeds and the like can be tested for the presence of this insert in the DNA.

Genomic Flanking Sequences

The plasmid shown in FIG. 9 contained the LB (left border) RB (the right border), the FMV 35S promoter (from a modified figwort mosaic virus), and the main gene of interest to give glyphosate resistance the CP4 syn: the 5-enolpyruvylshikimate-3-phosphate synthase (CP4 EPSPS) gene from Agrobacterium sp. Strain CP4. The plasmid also contains a chloroplast transit peptide and a terminator from pea. The circular vector pMON17227 opens at both left and right borders when inserted into the plant genome to form the transformed Event. The selected transformation event was the T227-1 Event. This transformed beet T227-1 and its progeny show excellent levels of glyphosate tolerance.

To characterize T227-1 fully, providing information that serves as a basis for event-specific PCR tests, the nucleotide sequences of the breakpoints between inserted vector and plant genomic DNA were determined.

Genomic sequences flanking the T227-1 insert were isolated by linker PCR. Genomic DNA was digested with restriction endonucleases and linkers attached to the ends of the fragments obtained. The fragments containing the T227-1 sequences were preferentially amplified by PCR using the linker sequence and pMON17227-specific sequences as primers. The PCR products were sequenced directly, and the sequences used to design further primers; these were then used to amplify plant genomic DNA from the T227-1 transformant for both left and right borders (flanking sequences PCR) and from an untransformed plant.

FIG. 1 shows the primers used in the flanking PCR test. The first pair of primers is in the right border region of the inserted material. 98k89 (nucleotides 155–180 of SEQ ID NO: 4) is a primer that is located within the sugar beet plant genome. 98I50 (nucleotides 455–476 of SEQ ID NO: 14) is a primer that is located in the inserted plasmid DNA sequence. In combination these primers can be employed to produce a unique piece of DNA through a PCR test. This unique DNA specifically identifies this T227-1 transformation event. The sugar beet identified by this PCR flanking sequence is only the T227-1 event or its progeny.

The second pair of primers is in the left border region of the inserted material. 98K86 (nucleotides 730–753 of SEQ ID NO: 10) is a primer that is located within the sugar beet plant genome. 98G94 (nucleotides 1–20 of SEQ ID NO: 15) is a primer that is located in the inserted plasmid DNA sequence. In combination these primers can be employed to produce a unique piece of DNA through a PCR test. These event-specific tests using the primers include a method that employs electrophoresis through gels as the standard method used to separate, identify, and purify DNA fragments. The location of the DNA that is separated by size within the gels can be determined by using a dye. This dye permits DNA bands with 1–10 ng of DNA to be detected under ultraviolet light. This unique DNA specifically identifies the T277-1 transformation event. The sugar beet identified by this PCR flanking sequence is only the T277-1 event or its progeny. Test kits comprising at least one set of primers wherein one such primer is located within the sugar beet plant genome proximate the insert and the other such primer is located within the inserted plasmid DNA sequence of T227-1, wherein a unique piece of DNA is capable of being identified wherein the material is identified as being GMO positive or GMO negative. Additionally, the material can be more specifically identified as being T277-1 or its progeny.

Primers 98K89 (nucleotides 155–180 of SEQ ID NO: 4) and 98K86 (nucleotides 730–753 of SEQ ID NO: 10) for the T277-1 event or its progeny are situated in the regions flanking the inserted sequences, while 98I50 (nucleotides 455–476 of SEQ ID NO: 14) and 98G94 (nucleotides 1–20 of SEQ ID NO: 15) lie inside the DNA from the vector. The resulting PCR products are described in Table 2.

TABLE 2

Specific primers inside and outside the integrated vector sequence.

| | Vector specific primer (position) | Flanking DNA primer | PCR product |
|---|---|---|---|
| Left border | 98G94 (2503 bp) (nucleotides 1–20 of SEQ ID NO: 15) | 98K86 nucleotides 730–753 of SEQ ID NO: 10 | 792 bp (SEQ ID NO: 15) |
| Right border | 98I50 (8232 bp) (nucleotides 455–476 of SEQ ID NO: 14) | 98K89 (nucleotides 155–180 of SEQ ID NO: 4) | 476 bp (SEQ ID NO: 14 |

PCR with these primers was performed on a 9600 thermocycler from PE-Biosystems. In each 50 μl reaction, 50 ng of plant DNA was incubated with 120 ng of each primer and 1U of Amplitaq DNA Polymerase in GeneAmp PCR buffer II containing 10 mM Tris-HCl pH8.3 and 50 mM KCl complemented with 1.5 mM $MgCl_2$ and 0.2 mM dNTP. One PCR reaction consisted of a hot start of 3 min. at 94° C. followed by 35 cycles (one cycle: 30 sec. at 94° C., 1 min. at 57° C. and 1 min. at 72° C.). The PCR products were separated on a 1.5% agarose gel.

This amplification clearly demonstrates that the left and right flanking sequences are normally contiguous in sugar beet, and have not suffered major reorganisation as a result of the transformation.

Flanking Sequences—Progeny of T227-1

By sequencing the flanking regions we developed specific primers from the left and right flanking sequences, and used these in PCR reactions with each other or individually with primers from within the insert. Such a PCR assay can be used to identify the T227-1 transformation event and its progeny uniquely.

Primer pairs (plant genomic DNA/plasmid DNA) for both the left and the right region were tested on T227-1, its progeny and the non-transformed lines. Both primer combinations gave positive results for all the glyphosate resistant plants (all generations). All these PCR products were identical to those obtained with transformation event T227-1. The fragment lengths of a few of the combinations are listed in FIGS. 10a–10c (SEQ ID NOS: 13–15). Other primer pairs can give different fragments. The glyphosate sensitive plants and the non-transformed line, however, showed no amplification product at all.

Figure 2:
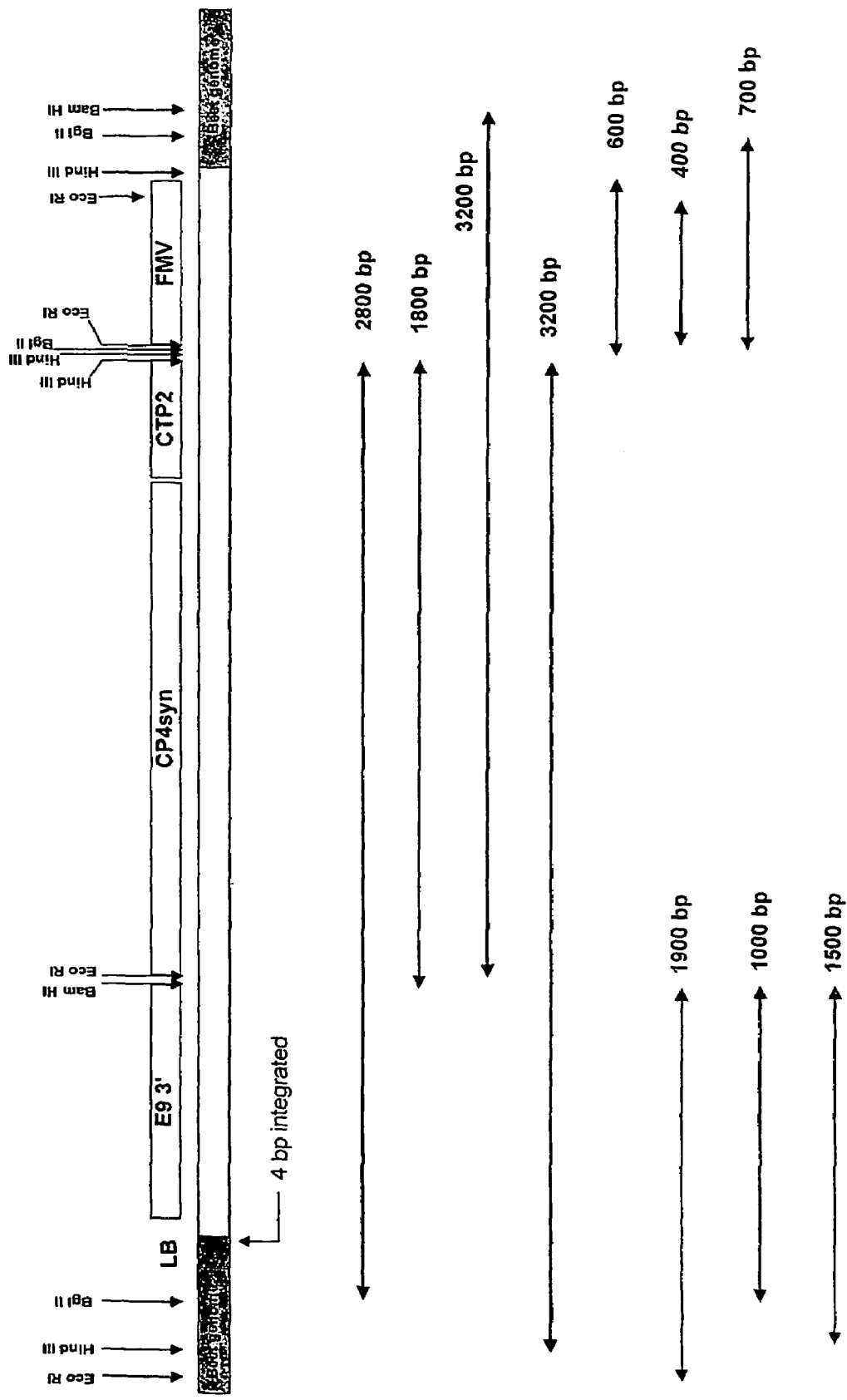
FIG. 2 shows the diagrammatic interpretation of the Southern blot results.

The T227-1 event and its progeny were tested for this unique DNA by using Southern blots. FIG. 2 shows the diagrammatic interpretation of the Southern blot results. The four boxes on top of the figure depict the plasmid sequence DNA that was incorporated into the transformed sugar beet T227-1. The components of the plasmid differ somewhat from the inserted material. The sugar beet was transformed through the use of *Agrobacterium*. Therefore, the plasmid contained both the right and left T-DNA border regions. The right T-DNA border sequence was not transformed into T227-1. The left T-DNA border sequence was not transformed except for a small 4 base pair section that is integrated between the sugar beet plant genome and the E9 3' terminator sequence.

The inserted material is identified as FMV, CTP 2, CP4 syn, E9 3', LB. FVM is a 35S promoter from a modified figwort mosaic virus. CP4 syn is the 5-enolpyruvylshikimate-3-phosphate synthase (CP4 EPSPS) gene from *Agrobacterium* sp. Strain CP4. CTP2 is the chloroplast transit peptide from *Arabidoposis*. E9 3' is the terminator. LB is the small portion of the left border sequence from *Agrobacterium*.

The vertical arrows depict the restriction sites located in the genome and the inserted material. The horizontal lines below the top two boxes depict the approximate number of base pairs that are in a fragment that is produced by employing the restriction enzyme indicated on the top box. The second box depicts the transformed sugar beets genetic makeup at the insert site.

The beet genomic sequences flanking this insert have been sequenced, and employed to design specific PCR tests for the T227-1 insertion. Flanking primers may be used for amplification of untransformed sugar beet DNA, indicating that the transformation did not induce any major rearrangements in the beet genome. This is confirmed by sequence analysis, which shows that the sequences on either side of the insert are essentially collinear with those of untransformed "alleles" from the same locus. Thus the present invention includes a method of using primers that identify T227-1 in a PCR method of detecting DNA. The invention also covers each of the two pair of primers that flank the right and left borders. The invention further covers the sugar beet having the DNA that is detectable by the primers.

We claim:

1. A pair of primers selected from the group consisting of:
    the pair of primers identified as 98G94, which consists of nucleotides 1–20 of SEQ ID NO: 15 and 98K86, which consists of nucleotides 730–753 of SEQ ID NO: 10 and;
    the pair of primers identified as 98I50, which consists of nucleotides 455–476 of SEQ ID NO: 14 and 98K89, which consists of nucleotides 155–180 of SEQ ID NO: 4.

2. A pair of primers of claim 1 that hybridizes to a transgenic insert of DNA of a transgenic glyphosate-resistant sugar beet, wherein the transgenic insert of DNA comprises at least one right border region, and at least one left border region, and comprises a figwort mosaic virus 35S promoter, DNA encoding a chloroplast transit peptide from the EPSPS gene of *Arabidopsis*, and an optimized CP4 EPSPS gene from *Agrobacterium* sp. CP4, and a terminator.

3. A pair of primers according to claim 2 comprising DNA which hybridizes to DNA that lies in the right border region of the insert DNA.

4. A pair of primers according to claim 2 comprising DNA which hybridizes to DNA that lies in the left border region of the insert DNA.

5. A pair of primers according to claim 3 or claim 4, wherein one primer of the pair comprises DNA which hybridizes to genomic DNA of the transgenic beet and the other primer hybridizes to the transgenic insert.

6. A method of detecting a transgenic sugar beet having an insert DNA comprising a figwort mosaic virus 35s promoter, a chloroplast transit peptide from the EPSPS gene of *Arabidopsis*, an optimized CP4 EPSPS gene from *Agrobacterium* sp. strain CP4 and a terminator; the method comprising the steps of:

1) amplifying DNA from the transgenic beet in the presence of a pair of primers selected from the group consisting of:
    the pair of primers identified as 98G94, which consists of nucleotides 1–20 of SEQ ID NO: 15 and 98K86, which consists of nucleotides 730–753 of SEQ ID NO: 10 and;
    the pair of primers identified as 98I50, which consists of nucleotides 455–476 of SEQ ID NO: 14 and 98K89, which consists of nucleotides 155–180 of SEQ ID NO: 4 using the polymerase chain reaction and 2) detecting the presence or the absence of the DNA fragment.

* * * * *

UNITED STATES PATENT AND TRADEMARK OFFICE
CERTIFICATE OF CORRECTION

PATENT NO. : 7,241,567 B2
APPLICATION NO. : 10/415602
DATED : July 10, 2007
INVENTOR(S) : G. Weyens et al.

It is certified that error appears in the above-identified patent and that said Letters Patent is hereby corrected as shown below:

| COLUMN | LINE | ERROR |
|---|---|---|
| 19 (Claim 1, | 4 line 3) | "15" should read --15,-- |
| 19 (Claim 1, | 5 line 4) | "NO: 10" should read --NO: 10;-- |
| 19 (Claim 1, | 6 line 5) | "and;" should read --and-- |
| 19 (Claim 1, | 8 line 7) | "14" should read --14,-- |
| 20 (Claim 6, | 5 line 3) | "chioroplast" should read --chloroplast-- |
| 20 (Claim 6, | 14 line 11) | "15" should read --15,-- |
| 20 (Claim 6, | 15 line 12) | "NO: 10" should read --NO: 10;-- |
| 20 (Claim 6, | 16 line 13) | "and;" should read --and-- |
| 20 (Claim 6, | 18 line 15) | "14" should read --14,-- |
| 20 (Claim 6, | 20 line 17) | "4" should read --4;-- |
| 20 (Claim 6, | 21 line 18) | "polyrnerase" should read --polymerase-- |

UNITED STATES PATENT AND TRADEMARK OFFICE
CERTIFICATE OF CORRECTION

PATENT NO. : 7,241,567 B2
APPLICATION NO. : 10/415602
DATED : July 10, 2007
INVENTOR(S) : G. Weyens et al.

It is certified that error appears in the above-identified patent and that said Letters Patent is hereby corrected as shown below:

| COLUMN | LINE | ERROR |
|---|---|---|
| 20 (Claim 6, | 21 line 18) | "reaction and" should read --reaction; and-- |

Signed and Sealed this

Eighteenth Day of December, 2007

JON W. DUDAS
*Director of the United States Patent and Trademark Office*